United States Patent [19]

Hudson et al.

[11] Patent Number: 5,425,380
[45] Date of Patent: Jun. 20, 1995

[54] SURGICAL EYE MASK

[75] Inventors: David M. Hudson, Atlanta; Jay R. Sommers, Marietta, both of Ga.

[73] Assignee: Kimberly-Clark Corporation, Neenah, Wis.

[21] Appl. No.: 306,218

[22] Filed: Sep. 14, 1994

Related U.S. Application Data

[63] Continuation of Ser. No. 52,800, Apr. 23, 1993, abandoned, which is a continuation of Ser. No. 708,597, May 31, 1991, abandoned.

[51] Int. Cl.⁶ ............................................. A61F 9/00
[52] U.S. Cl. ............................................. 128/858; 2/15
[58] Field of Search ................. 128/858, 863, 206.23, 128/206.24; 2/15, 171, 209.3, 426, 428, 439, 452

[56] References Cited

U.S. PATENT DOCUMENTS

| | | | |
|---|---|---|---|
| D. 292,410 | 10/1987 | Hunter | D16/102 |
| D. 311,012 | 10/1990 | Grange | D16/102 |
| D. 319,111 | 8/1991 | Sandel et al. | D29/9 |
| D. 319,451 | 8/1991 | Russell | D16/123 |
| D. 320,400 | 10/1991 | Hodges | D16/102 |
| D. 327,489 | 6/1992 | Kaye | D16/102 |
| 451,230 | 4/1891 | Williams | 2/443 |
| 583,590 | 6/1897 | Bennett | 2/452 |
| 988,081 | 3/1911 | Denman | 2/426 |
| 1,270,139 | 6/1918 | Fulford | 2/439 |
| 1,310,077 | 7/1919 | Heaford | 2/13 |
| 1,310,119 | 7/1919 | Harper | 2/452 |
| 1,824,908 | 9/1931 | Magee | 2/13 |
| 1,834,415 | 12/1931 | O'Meara | 2/13 |
| 1,947,137 | 2/1934 | Fraser | 2/439 |
| 2,368,303 | 1/1945 | Johnston | 2/426 |
| 2,568,316 | 9/1951 | Brown | 2/428 |
| 2,580,744 | 1/1952 | Edsall | 2/13 |
| 2,762,050 | 9/1956 | Bricker | 2/13 |
| 2,901,752 | 9/1959 | Granger | 2/13 |
| 3,023,418 | 3/1962 | Hammond | 2/13 |
| 3,171,134 | 3/1965 | Kennedy | 2/13 |
| 3,299,439 | 1/1967 | Bohner | 2/13 |
| 3,924,388 | 12/1975 | Morrison | 54/80 |
| 4,122,847 | 10/1978 | Craig | 2/15 |
| 4,122,847 | 10/1978 | Craig | 128/132 R |
| 4,502,156 | 3/1985 | Wishman | 2/DIG. 11 |
| 4,520,510 | 6/1985 | Daigle | 2/426 |
| 4,520,510 | 6/1985 | Daigle | 2/452 |
| 4,521,922 | 6/1985 | Mitchell et al. | 2/DIG. 11 |
| 4,698,852 | 10/1987 | Romero | 2/DIG. 11 |
| 4,720,415 | 1/1988 | Varder Wielen et al. | 428/152 |
| 4,779,291 | 10/1988 | Russell | 2/439 |
| 4,779,291 | 10/1988 | Russell | 2/439 |
| 4,790,031 | 12/1988 | Duerer | 2/15 |
| 4,796,621 | 1/1989 | Barle et al. | 128/206.23 |
| 4,833,734 | 5/1989 | Der Estephanian | 2/171 |
| 4,856,116 | 8/1989 | Sullivan | 2/DIG. 11 |
| 4,908,878 | 3/1990 | Tarragano | 2/15 |
| 4,908,878 | 3/1990 | Tarragano | 2/15 |
| 4,944,294 | 7/1990 | Borek, Jr. | 128/206.19 |
| 4,958,385 | 9/1990 | Rushton, Jr. | 2/DIG. 11 |
| 5,007,727 | 4/1991 | Kahaney et al. | 351/47 |
| 5,138,174 | 8/1992 | Smith | 2/9 |

FOREIGN PATENT DOCUMENTS

| | | |
|---|---|---|
| 1352 | 7/1903 | France . |
| 611458 | 9/1926 | France . |
| 378486 | 5/1922 | Germany . |
| 575231 | 5/1976 | Switzerland . |

OTHER PUBLICATIONS

Shieldmate Brochure.
Tecnol, Inc. Brochure.

*Primary Examiner*—Edgar S. Burr
*Assistant Examiner*—Aaron J. Lewis
*Attorney, Agent, or Firm*—Patrick C. Wilson

[57] ABSTRACT

Disclosed herein is an eye mask with a soft, comfortable frame assembly which makes it particularly well-suited for use in surgical, dental and healthcare related applications. In a preferred embodiment the eye mask has separated lenses attached to an elastic nonwoven frame to provide an adjustable fit for a wide variety of facial contours and eye spacings. The lenses may be provided with anti-glare and anti-fog treatments to maintain visual clarity during use. The frame may be breathable and treated to have specific areas of hydrophilicity and hydrophobicity so as to absorb perspiration and resist penetration of fluids splashed or sprayed onto the face during surgical procedures.

14 Claims, 2 Drawing Sheets

SURGICAL EYE MASK

This application is a continuation of application Ser. No. 08/052,800 entitled "SURGICAL EYE MASK" and filed in the U.S. Patent and Trademark Office on Apr. 23, 1993 now abandoned, which is a continuation of application Ser. No. 07/708,597 bearing the same title and filed in the U.S. Patent and Trademark Office on May 31,1991 now abandoned.

BACKGROUND OF THE INVENTION

The present invention relates to an eye mask. More specifically the eye mask is a goggle-type design which is very conformable to the face of the wearer and which can be worn behind a wearer's glasses if so desired. The primary area of use for the present invention is in the health care area and in particular hospitals, dental offices, doctor offices, clinics, labs and veterinary clinics. The eye mask is contemplated, however, to be useable in a wide variety of applications and, therefore, should not be limited to the above utilizations.

Eye protection is an important consideration in a number of areas not the least of which is the health care area. Physicians, dentists, nurses and hygienists are but a small portion of the health care personnel which are exposed to splashing fluids and small particle debris. Many times during surgical and dental procedures there are large amounts of fluid generated. Some of these fluids are body fluids while others are irrigation fluids. There are growing concerns that persons coming in contact with these fluids may have some degree of risk of contracting bacterial and viral diseases as a result of such contact. The eyes are considered one possible entry point for these diseases. As a result, more and more people are beginning to wear some form of eye protection. Some people simply wear glasses or large plastic/rubber safety goggles. Other people wear face shields much like a welder's mask or eye shields made from flexible plastic sheets such as Shieldmate (Pat. Pend.) (sold by AlphaProTech, Inc., Catalog/Model Nos. SM 2030, SM 2000, SM 2007, SM2015, SM 2035 and SM 2040). Yet another form of protection is a goggle/face mask combination as disclosed in U.S. Pat. No. 4,796,621 which has a low profile goggle attached to a face mask.

Glasses by themselves only provide protection from a frontal point of view as the areas around the glasses provide avenues for contaminants and fluid to enter the eyes. Goggles and safety glasses provide more protection, but are often cumbersome and uncomfortable to wear. In addition, such items are often difficult to wear in conjunction with prescription glasses. Full face shields, akin to welders' masks, are often cumbersome, sometimes fog due to containment of the wearer's breath and they still permit the entry of contaminants and fluids from the bottom side of the face shield. Similarly, partial face shields exhibit problems with unprotected paths to the eyes and difficulty in use with prescription glasses. As a result, it is an object of the present invention to provide an eye mask which exhibits both a good seal and a comfortable fit about the eye region of the wearer. It is another object of the present invention to provide an eye mask which has a flexible frame which is very soft to add to the comfort level of the wearer. Still a further object of the present invention is to provide an eye mask which is breathable to allow evaporation of perspiration and reduce fogging of the lenses. Yet another object of the present invention is to provide an eye mask which combines the above attributes in an eye mask with a stretchable or elastic frame assembly so that the mask readily conforms to the face and can be adjusted laterally for different width faces and eye spacing. These and other objects of the present invention will become more apparent upon a further review of the following specification, drawings and claims.

SUMMARY OF THE INVENTION

The present invention relates to a protective eye mask particularly suitable for use in health care applications. The protective eye mask is composed of a flexible frame assembly including a first and second eye opening separated by a bridge portion. Each of the eye openings includes a transparent lens which is sealingly engaged to the flexible frame assembly. To secure the protective eye mask about the face of the wearer, it is provided with securement means which are attached to opposite sides of the flexible frame assembly. The securement means may be elastic or inelastic and may be made from the same material as the frame assembly if so desired. To improve the fit of the protective eye mask, the bridge portion may be made from an expansible material, or the entire flexible frame assembly may be made elastic so that the distance between the eye openings of the eye mask may be tensionally adjusted to match the width of the mask to the spacing of the wearer's face.

Generally, the frame assembly should be of a sufficient size to completely cover the portion of the wearer's face surrounding the eyes, cheekbones and bridge of the nose. When the frame assembly is made elastic, it is preferred that the material for the frame assembly be a nonwoven laminate of at least one elastic layer bonded to at least one gatherable and non-elastic layer. To make the eye mask more versatile, the frame assembly may be formed with selected areas which are hydrophobic and other areas which are hydrophilic so that the mask can absorb perspiration and/or repel fluids that are splashed or sprayed onto the mask. The mask may also be made breathable so that it will allow perspiration to evaporate.

In yet another embodiment, the lenses may be attached to one another by a semi-rigid bridge portion which spans the bridge portion of the frame assembly. Lastly, the bridge portion of the frame assembly may be provided with a pleat to create a nose portion between the first and second eye openings to create a better fit.

DETAILED DESCRIPTION OF THE INVENTION

Figure 1:
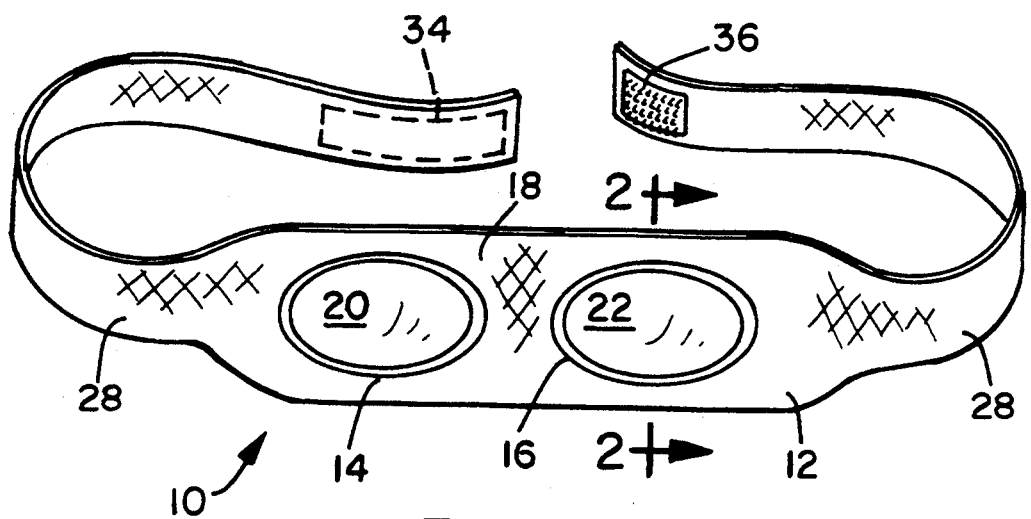
FIG. 1 is a perspective view of an eye mask according to the present invention.
Figure 2:
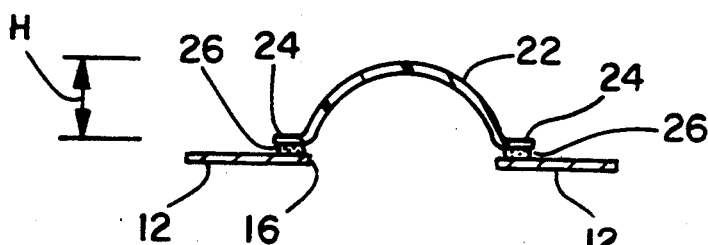
FIG. 2 is a cross-sectional view taken along line 2—2 of the eye mask of FIG. 1.

Referring to FIGS. 1 and 2 there is shown an eye mask 10 according to the present invention. The eye mask 10 comprises a frame assembly 12 including a first and second eye opening 14 and 16 respectively separated by an expansible bridge portion 18 for tensionally adjusting the distance between the first and second eye openings 14 and 16. Covering the eye openings 14 and 16 are a pair of transparent lenses 20 and 22 which are attached about their periphery 24 to the frame assembly 12 by attachment means 26 such as an adhesive or cement which is preferably flexible once cured or dried. Alternatively, the lenses 20 and 22 may be ultrasonically bonded to the frame assembly 12. To secure the eye mask 10 about the face of a wearer (not shown) there is provided securement means 28 attached to opposed sides of the frame assembly 12.

The frame assembly 12 should be a soft, flexible material such as a woven or nonwoven material. A preferred material is an elastic sheet material such as is disclosed in commonly assigned U.S. Pat. No. 4,720,415 which is incorporated herein by reference in its entirety. This material includes a laminate of at least one elastic layer bonded to at least one gatherable and non-elastic layer. The elastic web is bonded to the gatherable web at a plurality of spaced-apart locations in a repeating pattern and the gatherable web is gathered between the bonded locations. One of the advantages of such a material is its combination of elastic and softness properties to provide both comfort and fit. To achieve this combination it is helpful if the material has an elongation of at least about 25 percent to over 500 percent and an air porosity of at least about 1.05 seconds. Such materials can be generated using single-ply materials or laminates which include various combinations of strands, films and nonwovens which are elastic.

The composite elastic materials generally comprise at least one layer or web of elastic material bonded to one or more other layers of gatherable material, the elastic web being maintained in a stretched condition within its elastic range during the bonding step so that upon contracting or recovering after release of the stretching, i.e., elongating, tension force, the layer or layers to which it is bonded will gather or pucker. The resultant composite material is itself elastic, any of its non-elastic layers being able to move with the stretching of the elastic layer by reason of the play or give provided by the gathers formed, upon relaxation of the stretched elastic web, in the non-elastic layers to which the non-elastic web or webs are bonded. Composite materials made in accordance with the invention have shown remarkably good uniformity, hand, bulk, strength and elastic properties.

A wide variety of materials may be employed as the elastic web. As used herein, the terms "elastic" and elastomeric" have their usual broad meanings. However, for purposes of this invention "elastic" may be conveniently defined as follows. A material is elastic if it is stretchable to an elongation of at least about 25 percent of its relaxed length, i.e., can be stretched to at least about one and one-quarter times its relaxed length, and upon release of the stretching force will recover at least about 40 percent of the elongation, i.e., will, in the case of 25 percent elongation, contract to an elongation of not more than about 15 percent. For example, a 100 centimeter length of material will, under the foregoing definition, be deemed to be elastic if it can be stretched to a length of at least about 125 centimeters and if, upon release of the stretching force, it contracts, in the case of being stretched to 125 cm, to a length of not more than about 115 centimeters. Of course, many elastic materials used in the practice of the invention can be stretched to elongations considerably in excess of 25 percent of their relaxed length, and many, upon release of the stretching force, will recover to their original relaxed length or very close thereto. At least for some purposes of the present invention, elastic materials which upon release of the stretching force recover all or nearly all of their elongation are preferred. Elastic webs suitable for use in the invention include both elastic films and nonwoven fibrous elastic webs such as, for example, meltblown elastomeric fibrous webs. Such fibrous webs usually comprise "microfibers", which terms, as used herein means and includes fibers of a diameter not greater than about 100 microns, e.g., fibers of from about 1 to 50 microns in diameter, such as those which may be obtained by the meltblowing and spunbonding processes. In fact, nonwoven webs of meltblown microfibers constitute a preferred embodiment thereof. As used herein, "meltblown" microfibers refer to small diameter fibers, usually of a diameter not greater than about 100 microns, made by extruding a molten thermoplastic material as molten threads through a plurality of orifices into a high velocity gas (e.g., air) stream which entrains the extruded threads at their point of emergence from the orifices and attenuates the threads of molten thermoplastic material to reduce the diameter thereof, the gas stream-borne fibers then being deposited upon a collecting screen to form a coherent web of randomly dispersed fibers. Such a process is disclosed, for example, in U.S. Pat. No. 3,849,241, issued Nov. 19, 1974 to Robert R. Butin, et al.

The fibrous elastic web may also comprise a composite material in that it may be comprised of two or more individual coherent webs or it may comprise one or more webs individually comprised of a mixture of elastic and nonelastic fibers. As an example of the latter type of elastic web, reference is made to the aforementioned U.S. Pat. No. 4,209,563 in which elastomeric and non-elastomeric fibers are co-mingled to form a single coherent web of randomly dispersed fibers. Another example of such a composite web would be one made by a technique such as disclosed in U.S. Pat. No. 4,100,324 issued Jul. 11, 1978 to Richard A. Anderson, et al., and assigned to the assignee of this application. That patent discloses a nonwoven material comprised of a mixture of meltblown thermoplastic and other fibers which are combined in the gas stream in which the meltblown fibers are borne so that an intimate entangled co-mingling of thermoplastic meltblown fibers and other fibers, e.g., wood pulp or staple fibers, occurs prior to collection of the fibers upon a collecting device to form a coherent web of randomly dispersed fibers.

In some situations it may be desirable to make the frame assembly fluid-impervious through the use of films, coatings, hydrophobic nonwovens or hydrophobic treatments. This would most likely occur where strong liquid barrier properties are desired. When comfort is more of a concern, as with respect to perspiration and breathability, it may be more desirable to incorporate a microporous nonwoven meltblown layer into the frame assembly material to retard liquid penetration from the exterior surface (away from the user's face) while permitting perspiration to evaporate from the interior surface (next to the user's face). Evolution ® fabric, a spunbond-meltblown-spunbond nonwoven laminate sold by the Kimberly-Clark Corporation of Neenah, Wisconsin is one material which has such properties. To the same end it also may be desirable to make a material for the frame assembly which is hydrophilic on its interior surface and hydrophobic on its exterior surface. This can be done by the selection of the frame assembly materials or by the use of surface treatments such as surfactants to make the body-side surface hydrophilic.

Figure 5:
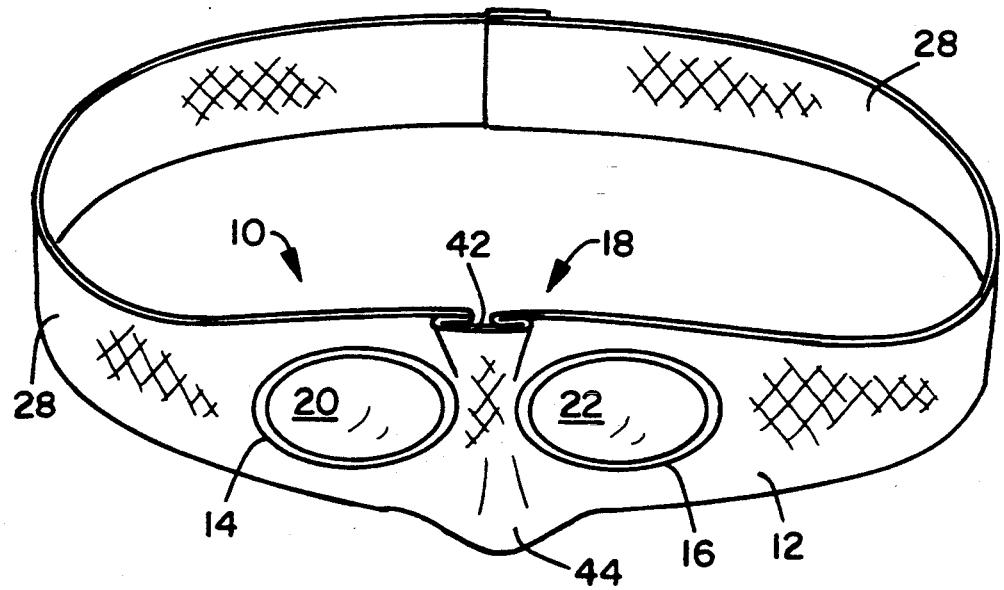
FIG. 5 is a perspective view of an eye mask according to the present invention with a continuous loop construction.

Referring to FIG. 5, to further increase fit, the frame assembly 12 may be fitted with a pleat 42 in the bridge portion 18 between the lenses 20 and 22 to create a nose portion 44. The pleat may be a single pleat (not shown) or a double pleat such as is shown in FIG. 5. A double pleat tends to lay flatter and is more comfortable against the bridge of the nose of the wearer. To secure the pleat, it may be ultrasonically or thermally bonded. Alternatively, it may be stitched, sewn, glued or taped.

The transparent lenses 20 and 22 are formed from an optically clear plastic using thermo-forming, injection molding or compression molding processes. Their shape may be round, elliptical or angular in shape so long as the optical clarity is good. In a preferred embodiment, it is desirable to keep the overall height H of the lenses below about 0.75 inches so that the eye mask 10 may be worn behind most glasses. One suitable material for forming the lenses is glycol modified polyethylene terephthalate. As shown in FIG. 2, the lenses 20 and 22 may include a peripheral lip 24 to provide a flat surface for the attachment of the lenses to the frame assembly 12 via the attachment means 26. If problems with glare and/or fogging are expected, the lenses 20 and 22 may be subjected to anti-glare and anti-fog treatments well known to those skilled in the art of optics. Preferably, the lenses are sealed about their entire periphery 24 for protection purposes. Hot melt adhesives work well, as does ultrasonic bonding, especially from a production/time standpoint. It is helpful though if the adhesive is pliable to aid the flexibility and fit of the overall eye mask 10.

Figure 3:
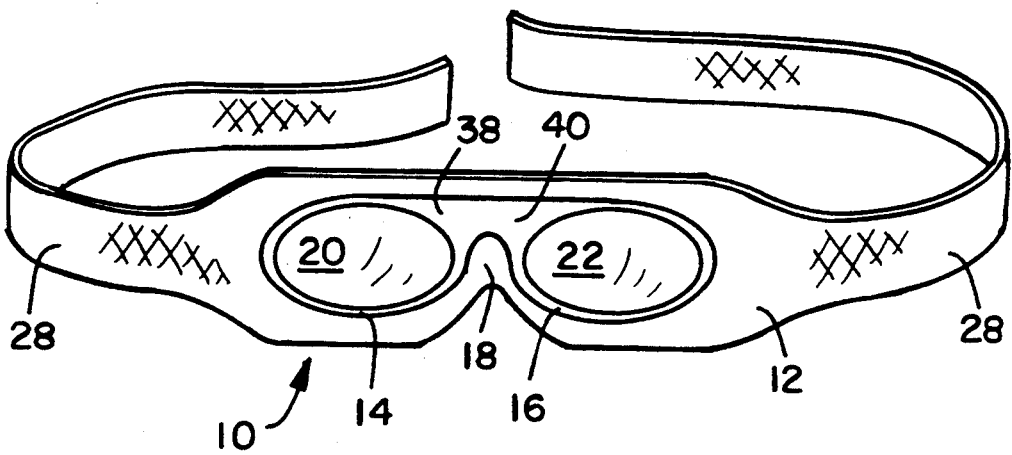
FIG. 3 is another perspective view of another eye mask according to the present invention having eye lenses attached to a common eye frame.
Figure 4:
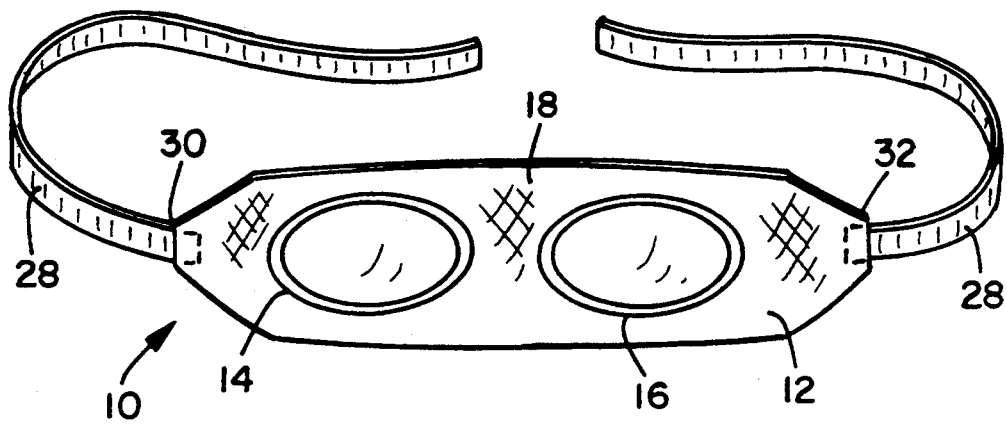
FIG. 4 is a perspective view of an eye mask according to the present invention with separate ties attached to either side of the eye mask.

The securement means 28 shown in FIGS. 1, 3 and 5 are actually made of the same material as the frame assembly 12 thereby yielding a one piece design. Alternatively, the securement means 28 may be made from a separate material and affixed to opposed sides 30, 32 of the frame assembly 12 as shown in FIG. 4. The securement means may be made from either an elastic or non-elastic material though elastic materials are preferred. The width of the securement means may be rather narrow such as is shown in FIG. 4 or, as shown in FIG. 5, it may be wider, in the range of about ½ inch to about 1½ inches, to provide more friction about the head of the wearer to reduce slippage and distribute the tensional forces over a wider portion of the head thereby reducing discomfort during prolonged surgical or other procedures.

The securement means 28 may be separate straps such as are shown in FIGS. 1, 3 and 4 which simply may be tied together at the back of the head of the wearer or they may be provided with fastening means 34, 36 such as hook and loop Velcro ® type material, snaps or other means. Alternatively, the securement means 28 may be fastened to one another such as shown in FIG. 5 to make a continuous loop with the frame assembly 12 so that the eye mask 10 can be tensionally worn about the wearer's head.

The eye mask 10 shown in FIGS. 1, 4 and 5 has lenses 20 and 22 which are independent of one another and separated by an expansible bridge portion 18. In FIG. 3 the lenses 20 and 22 are connected to one another by a lens frame 38 including a nose bridge portion 40. This embodiment tends to give a higher degree of support about the eyes of the wearer due to the lens frame 38.

With all of the embodiments shown in the figures, the major advantages are fit and comfort. The soft, elastic nature of the frame assembly 12 and securement means 28 gives excellent fit and conformity of the eye mask 10 about the eyes of the wearer thereby providing a good seal with the face. In addition, because of the low profile of the mask 10 and the ability of the bridge portion 18 to conform to the shape of the bridge of the wearer's nose, the mask can be worn underneath most glasses with the bridge portion 18 providing a good surface for the pads of a pair of glasses to rest upon. Lastly, because of the versatility of the frame assembly material, it can be made breathable and selectively hydrophilic and hydrophobic to absorb perspiration from the brow of the wearer while still retarding fluid penetration from the other direction. All of the features are in turn combinable in an eye mask which is low cost and therefore can be employed as a single use disposable item. Having thus described the invention in detail, it should be appreciated that various modifications and changes can be made in the present invention without departing from the spirit and scope of the following claims.

What is claimed is:

1. A protective eye mask comprising:
    a flexible fibrous nonwoven elastic frame assembly including a first and second eye opening separated by an expansible bridge portion for tensionally adjusting the distance between said first and second eye openings, said flexible fibrous nonwoven elastic frame assembly having a hydrophilic interior surface and a hydrophobic exterior surface, said flexible fibrous nonwoven elastic frame assembly comprising a laminate of at least one elastic fibrous layer bonded to at least one gatherable and non-elastic fibrous layer,
    transparent lenses located in said first and second eye openings, said lenses being sealingly engaged to said elastic frame assembly, and
    securement means attached to opposed sides of said elastic frame assembly for securing the eye mask about the eyes of the wearer.

2. The eye mask of claim 1 wherein said frame assembly is of sufficient size to completely cover the portion of a wearer's face surrounding the eyes, cheekbones and bridge of the nose.

3. The eye mask of claim 1 wherein said securement means is elastic.

4. The eye mask of claim 1 wherein said flexible fibrous nonwoven elastic frame assembly is made from a laminate of at least one elastic fibrous layer bonded to at least one gatherable and non-elastic fibrous layer.

5. The eye mask of claim 1 wherein said securement means form a continuous loop with said flexible fibrous nonwoven elastic frame assembly.

6. The eye mask of claim 1 wherein said expansible bridge portion further includes a pleat to create a nose portion between said first and second eye openings.

7. The eye mask of claim 1 wherein said at least one gatherable and non-elastic fibrous layer is bonded to said at least one elastic fibrous layer at spaced-apart locations, said at least one gatherable and non-elastic fibrous layer being gathered between said spaced-apart locations.

8. A protective eye mask comprising:

a flexible fibrous nonwoven elastic frame assembly including a first and second eye opening separated by an expansible bridge portion doe tensionally adjusting the distance between said first and second eye openings, said flexible fibrous nonwoven elastic frame assembly comprising a laminate of at least one elastic fibrous layer bonded to at least one gatherable and nonelastic fibrous layer, transparent lenses located in said first and second eye openings, said lenses being sealingly engaged to said elastic frame assembly, and securement means attached to opposed sides of said elastic frame assembly for securing the eye mask about the eyes of the wearer.

9. The eye mask of claim 8 wherein said frame assembly is of sufficient size to completely cover the portion of a wearer's face surrounding the eyes, cheekbones and bridge of the nose.

10. The eye mask of claim 8 wherein said securement means is elastic.

11. The eye mask of claim 8 wherein said securement means form a continuous loop with said flexible fibrous nonwoven elastic frame assembly.

12. The eye mask of claim 8 wherein said expansible bridge portion further includes a pleat to create a nose portion between said first and second eye openings.

13. The eye mask of claim 8 wherein said flexible fibrous nonwoven elastic frame assembly has a hydrophilic interior surface and a hydrophobic exterior surface.

14. The eye mask of claim 8 wherein said at least one gatherable and non-elastic fibrous layer is bonded to said at least one elastic fibrous layer at spaced-apart locations, said at least one gatherable and non-elastic fibrous layer being gathered between said spaced-apart locations.

* * * * *